United States Patent [19]

Hamann et al.

[11] Patent Number: 6,150,569
[45] Date of Patent: Nov. 21, 2000

[54] PROCESS FOR PREPARING LOWER AND HIGHER ALKALI METAL ALKOXIDES, IN PARTICULAR POTASSIUM TERT-BUTOXIDE, BY MICROHETEROGENEOUS CATALYSIS

[75] Inventors: Carl Heinz Hamann, Ovelgönne; Jörg Helling, Oldenburg; Peter Schmittinger, Unterhaching, all of Germany

[73] Assignee: Huels Aktiengesellschaft, Marl, Germany

[21] Appl. No.: 09/234,638

[22] Filed: Jan. 21, 1999

[30] Foreign Application Priority Data

Jan. 21, 1998 [DE] Germany ............... 198 020 13

[51] Int. Cl.$^7$ ....................................................... C07C 31/30
[52] U.S. Cl. ................................................................. 568/851
[58] Field of Search ............................................... 568/851

[56] References Cited

U.S. PATENT DOCUMENTS 5,262,133  11/1993  Adams ................................... 568/851

*Primary Examiner*—Michael L. Shippen
*Attorney, Agent, or Firm*—Oblon, Spivak, McClelland, Maier & Neustadt, P.C.

[57] ABSTRACT

A process for preparing an alkali metal alkoxides by reacting an alkali metal amalgams and alcohols in the presence of a catalysts comprising a transition metal carbide, nitride or carbonitride, where the catalyst is in the form of a powder.

31 Claims, No Drawings

PROCESS FOR PREPARING LOWER AND HIGHER ALKALI METAL ALKOXIDES, IN PARTICULAR POTASSIUM TERT-BUTOXIDE, BY MICROHETEROGENEOUS CATALYSIS

BACKGROUND OF THE INVENTION

1. Field of the Invention

The present invention relates to a process for the microheterogeneously catalyzed preparation of alkali metal alkoxides, in particular potassium tert-butoxide, from alkali metal amalgams and alcohols.

2. Background of the Invention

Alkali metal alkoxides, particularly of alcohols having up to 4 carbon atoms, are valuable chemicals. They are used, for example, as catalysts in the synthesis of many organic compounds. Here, chiefly the alkoxides of sodium and of potassium have achieved practical importance. A number of methods are known for preparing alkali metal alkoxides (see, F. A. Dickes, Ber. Dtsch. Chem. Ges. 63, 2753 [1930]). Solutions of alkali metal hydroxides in an alcohol contain alkali metal alkoxide in equilibrium. Removing the water present in this equilibrium, for example by distillation, gives pure alkali metal alkoxides. However, particularly in the case of low-boiling alcohols, this way of shifting the equilibrium requires a great deal of energy.

Pure alkali metal alkoxides are obtained directly by dissolving an alkali metal in the corresponding alcohol. Sodium and potassium react violently with lower aliphatic alcohols such as methanol and ethanol, evolving hydrogen. Higher alcohols such as propanols and butanols are preferably reacted with the alkali metals at above the melting point of the latter, if desired under pressure and with stirring.

However, alkali metal is an expensive starting material. It is more economical to use the liquid alkali metal amalgam obtained in chlor-alkali electrolysis by the mercury process as source of alkali metal.

The reaction of alkali metal amalgam with alcohols to give alkoxides and also the use of catalysts for this reaction are known.

The process disclosed in EP-A 0 177 768 enables the reaction between the amalgam and the alcohol to be carried out quite quickly. The reaction is carried out using a bed of granular anthracite whose surface is coated with heavy metal oxide or a mixture of heavy metal oxides. The amalgam and alcohol are fed in continuously in countercurrent and the products are taken off continuously.

These processes are, however, quite unsatisfactory. For example, only from 60 to 80% of the sodium introduced by means of the amalgam are reacted with methanol. A conversion of up to 100% in the preparation of MeONa is achieved only if the method of DE 196 21 466 is followed.

However, even now, the preparation of, for example, potassium tert-butoxide is only possible in an economically still unsatisfactory space-time yield, even when the reaction is carried out in an autoclave at 140° C. and 7 bar.

SUMMARY OF THE INVENTION

An object of present invention is to provide a process for preparing alkali metal alkoxides which overcomes the disadvantages of the processes described above.

This object has been achieved with a process for preparing an alkali metal alkoxide, by reacting an alkali metal amalgam and an alcohol in the presence of a catalyst comprising a transition metal carbide, nitride or carbonitride, wherein the catalyst is in the form of a powder, to form the alkali metal alkoxide.

Various other objects, features and attendant advantages of the present invention will be more fully appreciated as the same becomes better understood from the following detailed description.

DETAILED DESCRIPTION OF THE INVENTION

A process has been found for the catalytic preparation of alkali metal alkoxides from alkali metal amalgams and alcohols in which the reaction is carried out in the presence of powder catalysts comprising transition metal carbides, nitrides and carbonitrides. Particularly suitable transition metals are molybdenum and tungsten. The carbides of these metals are particularly preferred. When using, for example, $Mo_2C$ or $WC$, the reaction surprisingly proceeds at a satisfactory rate, even for tertiary alcohols (microheterogeneous catalysis).

The powder catalysts used preferably a mean particle diameter of from 1 to 10 $\mu$m, preferably 2 $\mu$m. This range includes all specific values and subranges therebetween, including 3, 4, 5, 6, 7, 8 and 9 $\mu$m.

Linear or branched aliphatic alcohols having from 1 to 5 carbon atoms are particularly suitable for the process of the invention. The alcohol may be methanol, ethanol, a propanol (inclusive of all isomers), a butanol (inclusive of all isomers), or a pentanol (inclusive of all isomers). Tert-butanol is particularly preferred.

Any alkali metal may be used. Sodium or potassium are preferred.

The reaction may be circulated at a temperature of 60 to 100° C. Preferably, the reaction is conducted at the boiling point of the alcohol, under reflux conditions.

Having generally described this invention, a further understanding can be obtained by reference to certain specific examples which are provided herein for purposes of illustration only and are not intended to be limiting unless otherwise specified.

EXAMPLES

Example 1

In a 2000 ml three-necked flask provided with heating mantel, precision glass stirrer, reflux condenser and $N_2$ inlet, 200 g of tert-butanol are admixed with 2 kg of potassium amalgam (0.32% by weight of K) and 20 g of $Mo_2C$ powder and heated under reflux. After a reaction time of about 20 hours and subsequent filtration of the alkaline phase, about 200 ml of potassium tert-butoxide solution having a $KOBu^t$ content of 14% and a KOH content of 1.4% were obtained

Example 2

In a 2000 ml round-bottomed flask, 2.7 kg of potassium amalgam were heated under reflux with 340 g of tert-butanol and 20 g of tungsten carbide powder for 17 hours. The amalgam reacted to an extent of about 38%. An alcoholic phase having a $KOBu^t$ content of 7.2% by weight and a KOH content of 1.6% by weight is formed.

Example 3

In a stirred reactor provided with water jacket, reflux condenser, $N_2$ inlet and magnetic stirrer, 100 g of sodium amalgam (0 2% by weight of Na) are reacted at 60° C. with 100 g of n-amyl alcohol in the presence of 3 g of Mo$_2$C powder (2 μm). After 3 hours, the entire amount of alkali metal has reacted.

Example 4

In an experimental arrangement corresponding to Example 3, 100 g of methanol reacted completely with 100 g of sodium amalgam (0 2% by weight of Na) in the presence of 1.2 g of Mo$_2$C powder (2 μm) within 1.7 minutes.

Obviously, numerous modifications and variations of the present invention are possible in light of the above teachings. It is therefore to be understood that within the scope of the appended claims, the invention may be practiced otherwise than as specifically described herein.

German Patent Application no. 198 020 13.9, filed Jan. 21, 1998, is incorporated herein by reference in its entirety.

What is claimed is:

1. A process for preparing an alkali metal alkoxide, comprising:
reacting an alkali metal amalgam and an alcohol in the presence of a catalyst comprising a transition metal carbide, nitride or carbonitride, wherein the catalyst is in the form of a powder with a mean particle diameter of 1 to 10 μm, to form the alkali metal alkoxide.

2. The process of claim 1, wherein the transition metal is molybdenum.

3. The process of claim 1, wherein the transition metal is tungsten.

4. The process of claim 1, wherein the catalyst comprises molybdenum carbide.

5. The process of claim 1, wherein the catalyst comprises tungsten carbide.

6. The process of claim 1, wherein the alcohol is an aliphatic alcohol having from 1 to 5 carbon atoms.

7. The process of claim 1, wherein the alcohol is methanol, ethanol, a propanol, a butanol, or a pentanol.

8. The process of claim 1, wherein the alcohol is tert-butanol.

9. The process of claim 1, wherein the alkali metal is sodium or potassium.

10. The process of claim 1, which is conducted at a temperature of 60° C. to 100° C.

11. The process of claim 1, which is conducted at the reflux temperature of the alcohol.

12. The process of claim 11, wherein the transition metal is molybdenum or tungsten.

13. The process of claim 12, wherein the catalyst comprises molybdenum carbide or tungsten carbide.

14. The process of claim 13, wherein the catalysts has a mean particle diameter of 1 to 10 μm.

15. The process of claim 14, wherein the alcohol is an aliphatic alcohol having from 1 to 5 carbon atoms.

16. The process of claim 15, wherein the alkali metal is sodium or potassium.

17. The process of claim 16, which is conducted at a temperature of 60° C. to 100° C.

18. The process of claim 17, which is conducted at the reflux temperature of the alcohol.

19. The process of claim 18, wherein the alcohol is tert-butanol.

20. A process for preparing an alkali metal alkoxide, comprising:
reacting an alkali metal amalgam and an alcohol in the presence of a catalyst comprising a transition metal carbide, nitride or carbonitride, other than tungsten carbide, wherein the catalyst is in the form of a powder, to form the alkali metal alkoxide.

21. The process of claim 20, wherein the transition metal is molybdenum.

22. The process of claim 20, wherein the transition metal is tungsten.

23. The process of claim 20, wherein the catalyst comprises molybdenum carbide.

24. The process of claim 20, wherein the alcohol is an aliphatic alcohol having from 1 to 5 carbon atoms.

25. The process of claim 20, wherein the alcohol is methanol, ethanol, a propanol, a butanol, or a pentanol.

26. The process of claim 20, wherein the alcohol is tert-butanol.

27. The process of claim 20, wherein the alkali metal is sodium or potassium.

28. The process of claim 20, which is conducted at a temperature of 60° C. to 100° C.

29. The process of claim 20, which is conducted at the reflux temperature of the alcohol.

30. The process of claim 29, wherein the transition metal is molybdenum or tungsten.

31. The process of claim 30, wherein the catalyst comprises molybdenum carbide.

* * * * *